United States Patent [19]

Philipp

[11] Patent Number: 4,559,934
[45] Date of Patent: Dec. 24, 1985

[54] FOREFOOT ELEVATING DEVICE FOR PERONEAL NERVE DYSFUNCTION CASES

[75] Inventor: Alexander Philipp, Garbsen, Fed. Rep. of Germany

[73] Assignee: C. Nicolai GmbH & Co. KG, Hanover, Fed. Rep. of Germany

[21] Appl. No.: 585,788

[22] Filed: Mar. 2, 1984

[30] Foreign Application Priority Data

Mar. 3, 1983 [DE] Fed. Rep. of Germany ....... 3307815

[51] Int. Cl.$^4$ ............................................... A61P 3/00
[52] U.S. Cl. .................................................. 128/80 E
[58] Field of Search ........................... 128/80 A–80 J, 128/80 DB, 165, 166, 166.5, 87 R

[56] References Cited

U.S. PATENT DOCUMENTS

| 3,504,668 | 4/1970 | Boudon | 128/80 R |
| 3,986,501 | 10/1976 | Schad | 128/80 E |
| 4,033,581 | 7/1977 | Sheppard | 128/80 E |
| 4,329,982 | 5/1982 | Heaney | 128/80 E |

Primary Examiner—Curtis R. Davis
Attorney, Agent, or Firm—Jacques M. Dulin

[57] ABSTRACT

The invention relates to a device for elevating the forefoot in cases of peroneal nerve dysfunction, comprising four main elements: (a) a sock firmly fitting the foot; (b) a special dorsal plate member of a flexible and elastically yielding material which is anatomically fitted to the dorsum of the foot and extends between the forefoot and the lower tibial zone, which plate member is fastened to the dorsal surface of the sock; (c) elastic connector means engaging the opposite ends of the plate adjacent the forefoot and tibial zone ends; and (d) means for restraining the elastic connector in close proximity to the plate. The device has the advantages of simplicity of construction, ability to adjust the angle of repose of the foot by tension adjustment of the elastic connector and to compensate for footwear weight. Further, it can be worn with or without normal shoes, is inconspicuous, is easy to put on and take off, is comfortable and provides lateral stability to the foot.

20 Claims, 4 Drawing Figures

FOREFOOT ELEVATING DEVICE FOR PERONEAL NERVE DYSFUNCTION CASES

BACKGROUND OF THE INVENTION

1. Field

The invention relates to a device for raising the forefoot in the case of dysfunction of the peroneal nerve by means of an elastic connector having adjustable bias tension means which acts between the forefoot and the lower leg.

2. Physiology Background—Peroneal Nerve Dysfunction

In the healthy human being a trouble-free course of walking or running movement occurs by the alternate raising and lowering of the forefoot. The raising of the forefoot is caused by the muscles and ligaments running in the dorsum of the foot; these are controlled by the peroneal nerve which is part of the autonomous nervous system. When a partial nerve paralysis occurs, such as frequently remains after a stroke or cerebral hemorrhage, or due to injuries consequent to an accident, for example, an interruption of the nerve conduction system, a dysfunction of the peroneal nerve often occurs resulting in neurological failures of the foot-raising muscles and ligaments. In persons handicapped in such a manner, the forefoot constantly hangs downward by reason of its weight. In order to avoid dragging of the toes on the ground and incessant stumbling when advancing the foot during walking or running movement, the knee must be abnormally lifted (steppage). Walking is slow and awkward; running is difficult, if not impossible.

3. Description of Prior Art Devices, Their Disadvantages and Need in the Art

A known device for raising the forefoot shown in *Medizinische Klinik*, 1955, 155, No. 49, page 2094, has a relatively rigid right-angle plate arranged under the sole of the foot and behind the fibula, which rigidly fixes the foot in its normal position. The fibula-side shank of the angle plate is joined to the lower leg of the handicapped person, for example, by a strap. The sole-side plate shank is worked into an orthopedic shoe inlay or directly into an orthopedic shoe.

This device has a number of disadvantages. Because the angle plate is relatively rigid, the foot is unchangeably fixed in a right-angled position. The lowering of the foot, which is still possible in the case of a dysfunction of the peroneal nerve, is severly hampered by this device, and thus unimpeded extension of the foot is impossible.

A further drawback of this device is that the handicappted person must exclusively use orthopedic shoes since the angle plate, due to its awkward dimensions, is impossible to be received in a normal shoe. Thus, the handicapped person cannot wear sandals or slippers, for example, in domestic surroundings, without unhampered movement.

Finally, this device is highly disadvantageous in cosmetic respects, since the orthopedic shoe modified with the right-angle plate appears antiquated and clumsy. That shoe contrasts sharply with a normal shoe worn on the other healthy foot. Moreover, it is uncomfortable to wear as a consequence of its great weight.

German Pat. No. 349,372 shows another known practice in which a boot is adapted with an elastic connection between the part surrounding the forefoot and the shaft enclosing the lower leg. The elastic connection consists of a strap and a rubber band, in which arrangement the bias tension by which the forefoot is raised is adjustable. This arrangement, too, has the disadvantage that it offers aid to the injured person only if he is actually wearing the shoe.

Accordingly, there is a clear need in the art for solving the problem of creating a device which is usable without a specially constructed shoe, and which is inconspicuous.

THE INVENTION

Purposes and Advantages

It is among the purposes of the invention to provide an improved device for raising the forefoot of persons having peroneal nerve dysfunction, the advantages of the device being simplicity of construction, the ability to adjust the angle of repose of the foot by tension adjustment, the ability to over-lift the foot to compensate for the weight of a shoe, the inconspicuousness of the device so that it can be worn with normal shoes, its cosmetically favorable aspect, the ability to use it in domestic situations and without shoes, the ease of putting-on and taking-off of the device, its comfort for the wearer, and its ability to laterally stabilize the foot.

It is another purpose of the invention to provide a 4-part peroneal nerve dysfunction foot-raising assembly which cooperatingly produces the advantages listed above, which parts comprise a reinforced elastic sock having pockets for receivingly engaging a resilient plate having elastic (spring-like) properties, the plate being ergonomically designed to fit the dorsal surface of the foot and stabilize it, elastic connector means to provide adjustable lifting bias tension, and connector restraining means to provide further tension adjustment and confine the connector into close proximity to the plate so the assembly can be worn in a normal shoe.

Still further and other purposes, features and advantages of the invention will be evident from the description which follows.

SUMMARY

The problem posed is solved in accordance with this invention by a specially-designed articulatable foot support assembly comprising four main elements: (a) a sock firmly fitting the foot; (b) a special dorsal plate member of a flexible and elastically yielding material which is anatomically fitted to the dorsum of the foot and extends between the forefoot and the lower tibial zone, which plate member is fastened to the dorsal surface of the sock; (c) an elastic connector engaging the opposite ends of the plate adjacent the forefoot and tibial zone ends; and (d) means for restraining the elastic connector in close proximity to the plate.

The arrangement of the plate member on the sock in accordance with the invention does justice to the anatomy of the foot, since the foot-raising and foot-lowering ligaments to be replaced by the device are present on the dorsum of the foot. Moreover, through the elasticity (or spring-like qualities) present in the plate member, it is possible to lower the foot, whereby the extension movement of the foot in walking is unhindered. Since the device including the sock is unitary, it possible to be used entirely without shoes, thus facilitating movement in a domestic environment. The device also permits the wearing of normal footwear, is comfortable to wear and is cosmetically inconspicuous.

Advantageously, the two ends of the plate member are seated in two pockets firmly sewn into or onto the sock. This permits easy insertion or removal of the plate member into the pockets. Putting on the sock is facilitated when the plate is removed since in practice it is simpler first to put on the sock without the plate and thereafter insert the plate in the pockets. The sock is more troublesome to put on when the plate is inserted first.

The sock consists of an elastic fabric which is reinforced in the heel region and in the region of the two pockets. Accordingly, the sock conforms firmly to the foot, and the reinforcements permit absorption of the forces exerted by the plate in walking.

As a further aspect of the invention, the elastic connector, which may be a relatively heavy rubber band, is guided in a middle zone between the plate-receiving end pockets by means of a restraining member. In one embodiment, lateral flaps protrude from a medial segment of the restraining member on both sides of the rubber connector band. The connector band extends above the restraining element by an adhesive strip or band, the free end of which passes over a crosspiece in the tibial end of the plate, is brought back toward the restraining member, and is fastened to itself or to the restraining member medial segment. Passing the adhesive band around the crosspiece and the use of an adhesive closure have the advantage that the rubber connector can be maintained at any desired preselected bias tension since the fastening points are distributed over the entire length of the band and are not restricted to one point.

It is convenient to provide the sock-facing surfaces of the two flaps of the restraining member with adhesive material so that they may be adjustably secured to the sock in a variety of desired positions. The restraining member holds the rubber connector band, which is tensioned in the manner of a tendon between the ends of the plate, close to the dorsal surface of the plate intermediate the foot portion and the tibial portion so that it does not interfere with a normal shoe or clothing and is otherwise not troublesome. Further, the restraining member causes an additional bias tension in the rubber connector band which can upwardly overstretch the foot. This overstretching is advantageous when a shoe is put on, since this overstretching of the foot is compensated for by the weight of the shoe so that the foot with the shoe on again occupies its normal position.

In another embodiment of the invention, the elastic connector comprises two rubber connector bands crisscrossed in an X-configuration. The two connector bands are each securely fastened at one end, laterally spaced one from the other, to the forefoot end of the plate. The other end of each has an adjustable buckle having a snap fastener cooperating with a cooperating snap element mounted on the dorsal face of the end of the plate, similarly laterally spaced from one another. In this arrangement the two rubber bands are arranged crossed from one end of the plate to the other end. This embodiment has the advantage of better lateral stabilization for the foot.

It is preferable to dispose an eyelet in the middle zone of the plate through which the rubber connector bands are passed in close proximity to the plate. Such an eyelet has the advantage that it tethers the bands at their crossover point, while having a low projection profile that does not interfere with a shoe.

BRIEF DESCRIPTION OF THE DRAWINGS

The invention is explained in detail below by reference to preferred embodiments which are represented in the drawings.

In the Drawings.

DESCRIPTION OF THE PREFERRED EMBODIMENTS

The following detailed description of the preferred embodiments is by way of example and not by way of limitation of the principles of the invention, and makes reference to the device represented in the figures.

Figure 1:
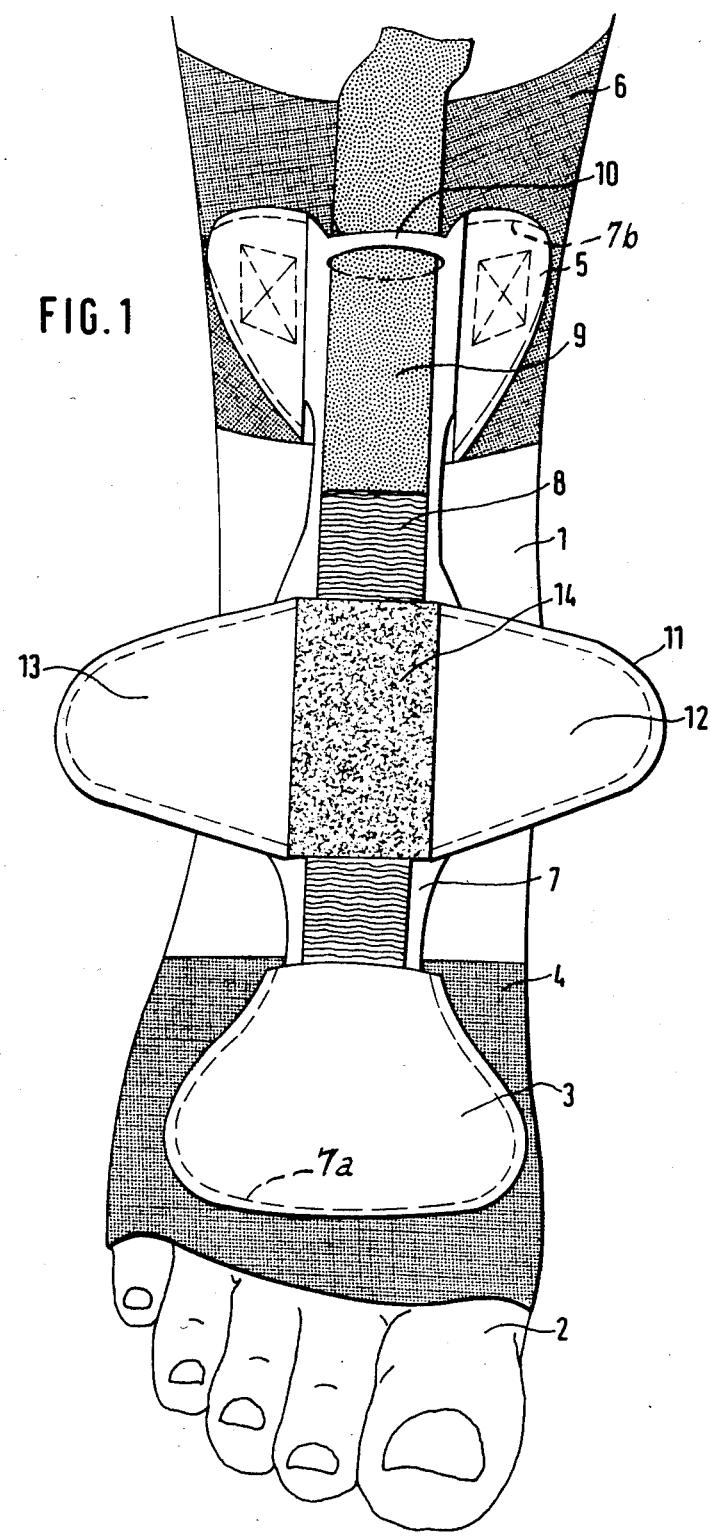
FIG. 1 shows a front elevation view of a first embodiment of the device in which the restraining member and the rubber connector band are not yet fastened.

FIG. 1 shows a sock 1, drawn over a foot 2, which sock, by reason of its elasticity, fits tightly on the foot. The elasticity is achieved in the same manner as support stockings by use of transversely and longitudinally running rubber threads. At the forefoot end, the sock 1 is open in order to prevent the toes from being constricted in their freedom of movement by the firmly contacting sock, and to prevent premature wearing-out of the sock by the toenails. A pocket 3 is secured (as by stitching) onto or into the dorsal surface of the foot portion of the sock. The fabric of the sock is reinforced in the region 4 surrounding the pocket 3 in order to adequately support the pocket 3. A second pocket 5 is sewn on the dorsal surface of the tibial portion of the sock, which is likewise reinforced in adjacent zone 6. Pockets 3 and 5 receivingly engage the ends 7a and 7b of a plate 7 made of an elastically yielding material, for example, a plastic such as that known under the trade name "Ortholen", or steel. As shown in FIG. 1 the pockets 3 and 5 are sewn on over the ends of the plate so that the plate is permanently secured to the stocking. In the alternative, the form of the plate ends and of the pockets can be adapted to one another so that the plate is removably insertable in the pockets. In practice it has proved that the insertable type plate facilitates handling since a plate permanently joined with the sock makes it difficult to put on or take off the sock. On the other hand, the insertion of the plate into the elastic sock after it is on presents no difficulties. In the case of the insertable plate, however, it is necessary to prevent the plate from slipping out of the pocket 5 by the bending or stretching movement of the lower leg during walking. This is provided for by a closure device (not shown) which comprises, for example, two bands gripping the ends of plate 7 in the zones of the pockets 3 and 5. These may be an adhesive closure or a pressure closure (such as a strap or wide rubber band).

Figure 2:
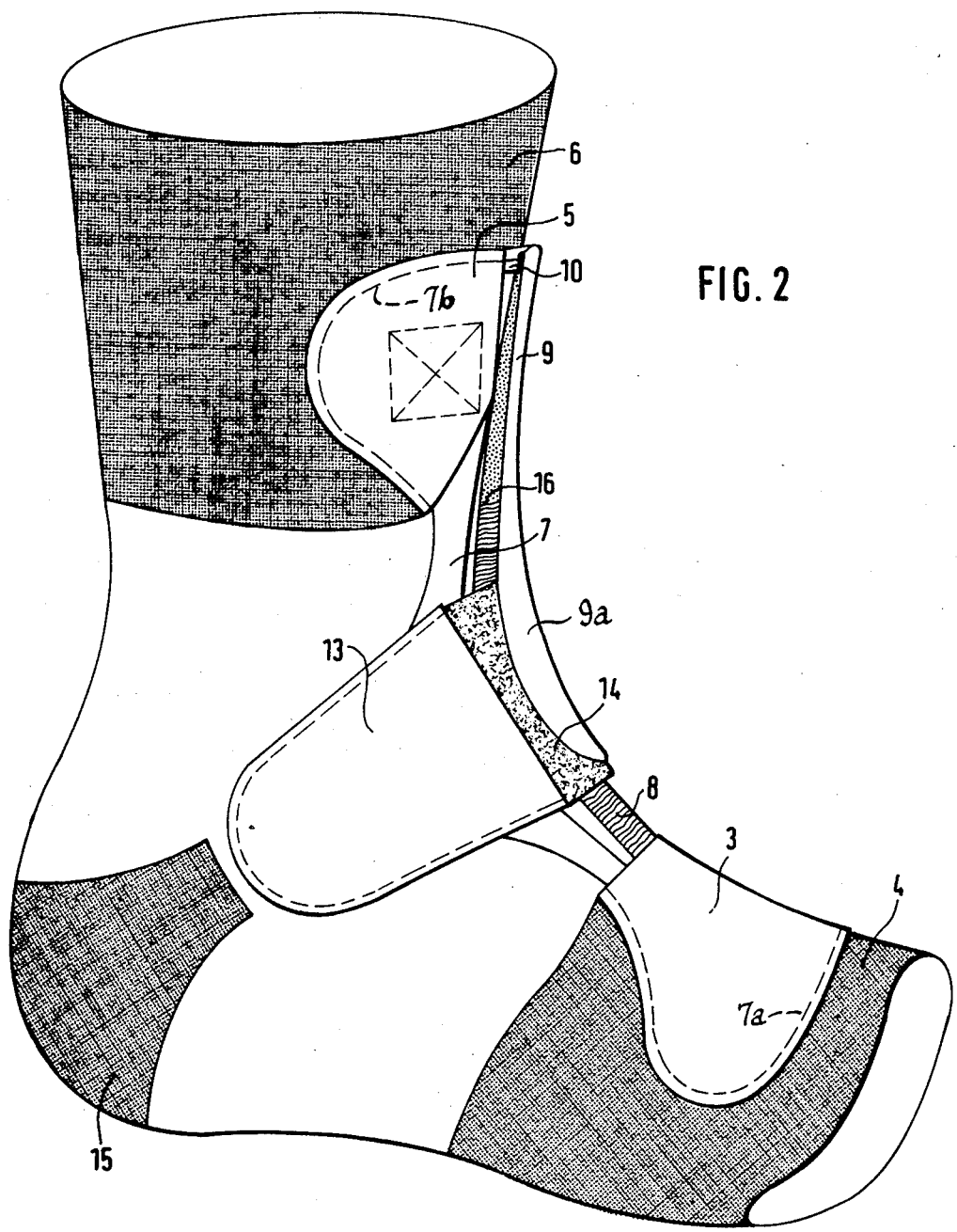
FIG. 2 shows a side elevation view of the device with restraining member and rubber connector fastened.
Figure 3:
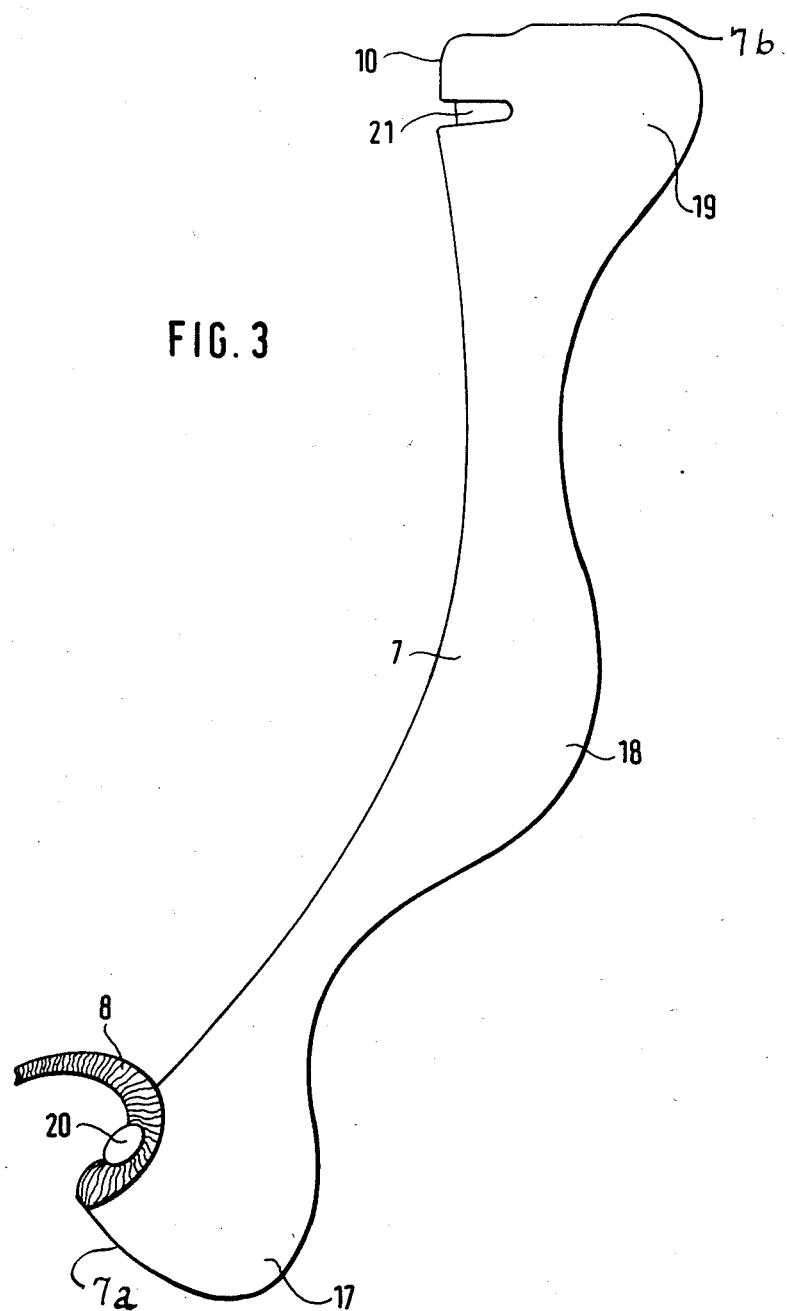
FIG. 3 shows a side elevation view of the plate.

As is best seen in FIG. 3, on the dorsal surface of the forefoot end of the plate 7 there is fastened a rubber connector band 8, one end of which has an adhesive band extension 9 (see FIGS. 1 and 2). The rubber connector band 8 and the adhesive band 9 extend to the tibial end of the plate 7. Slit 21 adjacent the tibial end forms a crosspiece 10 (FIG. 3), so that the adhesive band 9 can be threaded through the slit 21 about the crosspiece 10, and folded back in the direction of the foot end to overlie the band and adhesive band (see portion 9a of band 9 in FIG. 2). The rubber connector band 8 and the adhesive band 9 form in practice a "mechanical tendon" between the foot end 7a and the tibial end 7b of the plate 7.

In a middle zone between the foot and tibial ends of the plate 7, the rubber connector band 8 is passed under a restraining means 11. The length of the rubber connector band is dimensioned so that its upper end extends above restraining means 11. In FIGS. 1–3 the restraining means 11 is shown as comprising a pair of flaps 12, 13 extending laterally on both sides of the rubber connector band 8. The flaps are joined by a medial part 14, the upper side of which has a cloth-like surface so that the adhesive band 9 led back around the crosspiece 10 can be adhered thereto. The restraining member 11 is initially freely shiftable up or down on the rubber connector band 8. The ventral surfaces of the flaps 12 and 13 (i.e., the surfaces facing the sock 1) are provided with adhesive material so that the flaps 12 and 13 can be secured to the sock in any predetermined desired position.

FIG. 1 shows the stage in which the sock is stretched over the foot, but before the forefoot has been brought into its raised position.

The use of the device of the invention proceeds as follows. After the sock 1 is pulled on, and, in the case of an insertable plate, the ends 7a and 7b of plate 7 have been inserted in their respective pockets 3 and 5, the adhesive band 9 forming the extension of the rubber connector band 8 (which passes under or through the restraining means 11) is threaded through the slit 21 (see FIG. 3) and brought back around the crosspiece 10 to the medial part 14 of the restraining means 11 (see FIG. 2). By this process the rubber connector band is tensioned in such a way that the foot is lifted into its normal position in which it forms virtually a right angle to the lower leg. Upon selecting the appropriate bias tension as determined by the desired foot angle, the end portion 9a of the adhesive band is pressed onto the medial zone 14 of the fixing element (see FIG. 2), and the foot is thereby supported in its normal position.

The self-inhibiting action of the adhesive band in the zone of the crosspiece 10 of the plate 7 prevents the restraining means 11 from yielding to the tension of the rubber connector band 8. If need be, however, the restraining means 11 may be held fast by hand adjustment of the tension of band 8, and adhering the adhesive band portion 9a to the adhesive band 9, the connector band 8, and the medial segment 14.

Then the flaps 12 and 13 of the restraining means 11 are drawn (one in each hand) in the direction of the dorsum of the foot and pressed onto the sock 1 and secured to it by the adhesive material (see FIG. 2). Two things are achieved by this flap-securing step. First, the rubber connector band is made to confirm virtually completely to the curved form of the plate 7 and is no longer in the way. Second, the rubber connector band 8 is additionally tensioned, whereby the forefoot is lifted somewhat upwardly of its normal angle of repose. This lifting is useful when thereafter a shoe is put on, as this additional lifting of the forefoot is cancelled by the weight of the shoe.

FIG. 2 shows a reinforcement 15 in the heel zone of the sock which serves the purpose of absorbing forces exerted by the restraining means 11.

From FIG. 2 it is to be seen that in the final state the device of the invention hardly protrudes, so that normal footwear can be worn. This is an extraordinary advantage for the injured person both in practical and also in cosmetic respects.

The side view of the plate 7 in FIG. 3 shows that the plate 7 is constructed in such a way that in the zones 17, 18 and 19, the plate is provided with widened arches which are adapted to the anatomical form of the dorsum of the foot. The plate can thereby exert a strongly stabilizing function, which stabilizingly counteracts the lateral deflections of the foot which occasionally occurs in dysfunctions of the peroneal nerve. The widened arch end zones 17 and 19 are received by the two pockets 3 and 5 fastened to the sock (FIGS. 1 and 2). The rubber connector band 8 is fastened adjacent the foot end of the plate 7 by a rivet 20 or the like.

Figure 4:
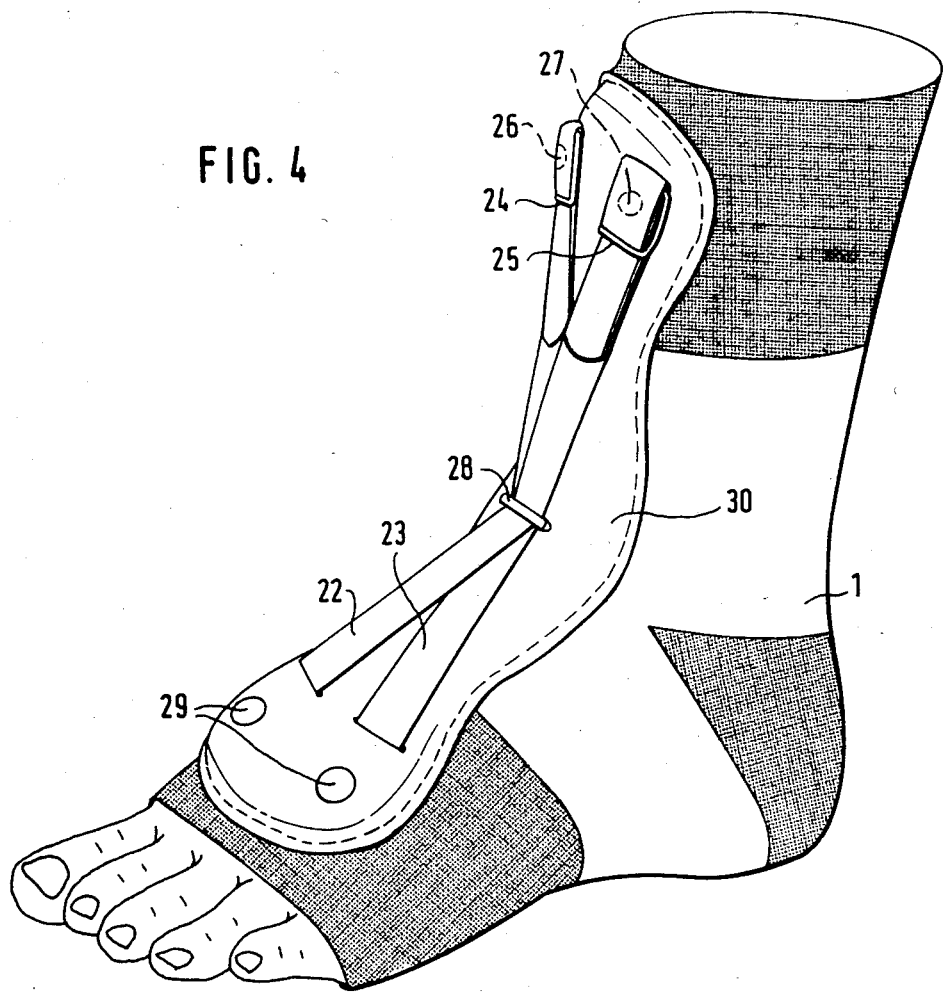
FIG. 4 shows in perspective a view of a second embodiment employing dual connector bands arranged in a X-configuration, tension adjustment buckles, and snap fasteners.

In the embodiment represented in FIG. 4, the plate 7 is permanently joined to the sock 1 over its entire length by a leather flap 30 which fully covers the plate and is sewn onto the sock so that the plate is not visible.

The rubber connector comprises in this embodiment an assembly of two rubber bands 22 and 23, the ends of which are laterally spaced from one another and fastened to the forefoot end of the plate, for example, by rivets 29. Adjacent the tibial ends of the rubber bands 22 and 23 there are arranged in each case an adjustment buckle 24 and 25, respectively. The buckles are constructed in the manner of belt buckles so that the length of the rubber connector bands is adjustable and thereupon fixable by threading through the buckle. The buckles 24 and 25 have one part of a snap fastener 26 and 27, respectively, while the two mating parts of the snap fastener are secured to the leather flap, correspondingly laterally spaced.

An eyelet 28 is disposed in the middle zone of plate 7 through which the two rubber connector bands 22 and 23 are threaded so that in the region of the eye they are confined close to the surface of the plate.

By the lateral spacing of their ends, the rubber connector bands 22 and 23 are criss-crossed from one end of the plate to the other.

The use of two connector bands 22, 23 has the advantage that there are two engagement points for the tensile force lying spaced from one another at both ends of the plate 7, resulting in better lateral stabilization for the foot.

It should be understood that various modifications within the scope of this invention can be made by one or ordinary skill in the art without departing from the spirit thereof. I therefore wish my invention to be defined by the scope of the appended claims as broadly as the prior art will permit, and in view of this specification if need be.

I claim:

1. Apparatus for elevating the forefoot in peroneal dysfunction cases comprising in operative combination:
    (a) a sock adapted to tightly fit the foot of the user;
    (b) a plate anatomically conforming to the dorsal surface of the foot having a forefoot end and a tibial end;
    (c) said dorsal plate being disposed in engagement with a dorsal surface of the sock;
    (d) said dorsal plate having spring-like properties of elastic yieldability;
    (e) elastic connector means disposed connectably adjacent the forefoot end and tibial end of said dorsal plate;

(f) said elastic connector means providing an adjustable bias tension between the forefoot and lower tibial portion of the user's leg; and
(g) said assembly in combination permitting: use with or without normal footwear, overtensioning to compensate for footwear weight, adjustment of the angle of respose of the foot, and lateral foot stability.

2. Forefoot elevating apparatus as in claim 1 wherein:
(a) said dorsal plate forefoot and tibial ends are permanently disposed in pockets sewn onto the sock.

3. Forefoot elevating apparatus as in claim 1 wherein:
(a) said dorsal plate forefoot and tibial ends are removably insertable into engagement with pockets disposed on said sock dorsal surface.

4. Forefoot elevating apparatus as in claim 1 wherein:
(a) said sock comprises an elasticized fabric having reinforcements disposed in the heel region and in the regions of engagement of said dorsal plate with said sock dorsal surface.

5. Forefoot elevating apparatus as in claim 2 wherein:
(a) said sock comprises an elasticized fabric having reinforcements disosed in the heel and pocket regions of said sock.

6. Forefoot elevating apparatus as in claim 1 which includes:
(a) means for restraining said elastic connector means medial of said forefoot and tibial ends of said dorsal plate into close proximity with said dorsal plate and to prevent projection of said elastic connector a substantial distance away from the medial section of said dorsal plate.

7. Forefoot elevating apparatus as in claim 2 which includes:
(a) means for restraining said elastic connector means medial of said forefoot and tibial ends of said dorsal plate into close proximity with said dorsal plate and to prevent projection of said elastic connector a substantial distance away from the medial section of said dorsal plate.

8. Forefoot elevating apparatus as in claim 3 which includes:
(a) means for restraining said elastic connector means medial of said forefoot and tibial ends of said dorsal plate into close proximity with said dorsal plate and to prevent projection of said elastic connector a substantial distance away from the medial section of said dorsal plate.

9. Forefoot elevating apparatus as in claim 4 which includes:
(a) means for restraining said elastic connector means medial of said forefoot and tibial ends of said dorsal plate into close proximity with said dorsal plate and to prevent projection of said elastic connector a substantial distance away from the medial section of said dorsal plate.

10. Forefoot elevating apparatus as in claim 5 which includes:
(a) means for restraining said elastic connector means medial of said forefoot and tibial ends of said dorsal plate into close proximity with said dorsal plate and to prevent projection of said elastic connector a substantial distance away from the medial section of said dorsal plate.

11. Forefoot elevating apparatus as in claim 6 wherein:
(a) said restraining means comprises a pair of laterally protruding flaps joined by a medial segment;
(b) said elastic connector has attached to its upper free end an adhesive band;
(c) said dorsal plate includes a slit disposed adjacent its upper tibial end to provide a crosspiece;
(d) said adhesive band is threaded through said slit, over said crosspiece, and is adjustably secured to said medial segment to provide a desired amount of bias tension.

12. Forefoot elevating apparatus as in claim 11 wherein:
(a) said flaps have on their ventral surfaces an adhesive material permitting them to be adjustably secured to said sock.

13. Forefoot elevating apparatus as in claim 3 wherein:
(a) said restraining means comprises a pair of laterally protruding flaps joined by a medial segment;
(b) said elastic connector has attached to its upper free end an adhesive band;
(c) said dorsal plate includes a slit disposed adjacent its upper tibial end to provide a crosspiece;
(d) said adhesive band is threaded through said slit, over said crosspiece, and is adjustably secured to said medial segment to provide a desired amount of bias tension.

14. Forefoot elevating apparatus as in claim 13 wherein:
(a) said flaps have on their ventral surfaces an adhesive material permitting them to be adjustably secured to said sock.

15. Forefoot elevating apparatus as in claim 1 wherein:
(a) said elastic connector means comprises a pair of rubber bands disposed in a cross-crossed X-configuration with opposite upper and lower ends laterally spaced from one another;
(b) each of said upper ends of said bands being threaded through a buckle adapted to be removably securable by snap fastener elements disposed laterally spaced apart adjacent the tibial end of said dorsal plate.

16. Forefoot elevating apparatus as in claim 12 wherein:
(a) said elastic connector means comprises a pair of rubber bands disposed in a criss-crossed X-configuration with opposite upper and lower ends laterally spaced from one another;
(b) each of said upper ends of said bands being threaded through a buckle adapted to be removably securable by snap fastener elements disposed laterally spaced apart adjacent the tibial end of said dorsal plate.

17. Forefoot elevating apparatus as in claim 6 wherein:
(a) said restraining means comprises an eyelet through which said elastic connector means is passed.

18. Forefoot elevating apparatus as in claim 17 wherein:
(a) said elastic connector means comprises a pair of rubber bands disposed in a criss-crossed X-configuration with opposite upper and lower ends laterally spaced from one another;
(b) each of said upper ends of said bands being threaded through a buckle adapted to be removably securable by snap fastener elements disposed laterally spaced apart adjacent the tibial end of said dorsal plate.

19. Forefoot elevating apparatus as in claim 18 wherein:
 (a) said dorsal plate is secured to the sock over its entire length.

20. Forefoot elevating apparatus as in claim 1 wherein:
 (a) said dorsal plate is adapted with arcuate flange portions, as seen both in elevation and cross-section, adjacent the forefoot and tibial ends and medially thereof to provide additional lateral stability to the user's foot.

* * * * *